United States Patent
Pratt et al.

(10) Patent No.: US 10,006,881 B2
(45) Date of Patent: Jun. 26, 2018

(54) MICROELECTRODES FOR ELECTROCHEMICAL GAS DETECTORS

(71) Applicant: LIFE SAFETY DISTRIBUTION AG, Hegnau (CH)

(72) Inventors: Keith Francis Edwin Pratt, Portsmouth (GB); John Chapples, Portsmouth (GB); Martin Geoffrey Jones, Havant (GB)

(73) Assignee: Life Safety Distribution AG, Hegnau (CH)

( * ) Notice: Subject to any disclaimer, the term of this patent is extended or adjusted under 35 U.S.C. 154(b) by 547 days.

(21) Appl. No.: 14/275,037

(22) Filed: May 12, 2014

(65) Prior Publication Data

US 2014/0353156 A1 Dec. 4, 2014

Related U.S. Application Data

(60) Provisional application No. 61/830,392, filed on Jun. 3, 2013.

(51) Int. Cl.
*G01N 27/407* (2006.01)
*G01N 27/404* (2006.01)

(52) U.S. Cl.
CPC ......... *G01N 27/407* (2013.01); *G01N 27/404* (2013.01)

(58) Field of Classification Search
CPC ............... G01N 27/30; G01N 27/413; G01N 27/404–27/409; B01D 53/22; B32B 37/00
See application file for complete search history.

(56) References Cited

U.S. PATENT DOCUMENTS

| | | | |
|---|---|---|---|
| 6,262,264 B1 * | 7/2001 | Buck, Jr. ............ | C07F 15/0026 205/792 |
| 2002/0121438 A1 | 9/2002 | Saffell et al. | |
| 2008/0277290 A1 * | 11/2008 | Jones ................ | B01J 21/18 205/775 |
| 2011/0100813 A1 * | 5/2011 | Davis ................ | G01N 27/40 204/415 |
| 2011/0226619 A1 | 9/2011 | Eckhardt et al. | |

FOREIGN PATENT DOCUMENTS

| | | |
|---|---|---|
| CN | 104215676 A | 12/2014 |
| EP | 2 498 085 A2 | 9/2012 |
| EP | 2811291 A2 | 12/2014 |
| WO | 2010063624 A1 | 6/2010 |

OTHER PUBLICATIONS

Le et al. (Electrochemical and Solid-State Letters, 15 (2) A19-A22 (2012)).*

(Continued)

*Primary Examiner* — Gurpreet Kaur
(74) *Attorney, Agent, or Firm* — Wick Phillips Gould & Martin, LLP

(57) ABSTRACT

An electrochemical gas sensor having an electrode with a catalyst distributed on a porous surface is described. The porous surface can be a polytetrafluoroethylene tape. Alternate embodiments include layered or stacked electrodes.

15 Claims, 6 Drawing Sheets

(56) References Cited

OTHER PUBLICATIONS

Extended European search report from corresponding EP application 14169751.6, dated Feb. 4, 2015.
He et al., Proton conductivity of phosphoric acid doped polybenzimidazole and its composites with inorganic proton conductors.
Journal of Membrane Science, Dec. 1, 2003, pp. 169 to 184, vol. 226, Lyngby, Denmark.
CAVIARE™ Nanoband Array, Platinum 303D (NP3003) [retrieved on Oct. 9, 2017] Retrieved from the Internet <https://www.nanoflex.com/Products/Research-Electrodes/Platinum-303D-Nanoband-(316SS)/9-332/NP3003-CAVIARETM-Nanoband-Array-Platinum-303D>. 2 pages.
Europe Patent Application No. 14169751.6, Partial European Search Report, dated May 6, 2015, 4 pages.
Kirsi Wallgren, PhD thesis, University of Nottingham, 2005.
Chinese Office Action; Application No. 20140325566.1; dated Sep. 11, 2017; 13 pages.
Wallgren, Kirsi; "Novel Amperometric Gas Sensors"; PhD Thesis; University of Nottingham; Jan. 2005; 205 pages.

\* cited by examiner

MICROELECTRODES FOR
ELECTROCHEMICAL GAS DETECTORS

CROSS REFERENCE TO RELATED
APPLICATION

This application claims priority of U.S. Provisional Application Ser. No. 61/830,392 filed Jun. 3, 2013, whose disclosures are incorporated herein by reference.

FIELD

This application pertains to electrochemical gas detectors, which incorporate microelectrodes. More particularly, this application pertains to electrochemical gas detectors, which include an electrode comprised of a catalyst deposited onto a porous surface.

BACKGROUND

Electrochemical gas sensors using microelectrodes have a number of benefits, such as the ability to use fast scanning voltammetric measurements, utilizing features such as convergent diffusion and potentially being simpler to construct than conventional gas diffusion electrodes. However they also suffer from disadvantages. In particular it is more difficult to achieve a reliable 3-phase region, i.e., a region where gas does not have to diffuse a long distance through the electrolyte before reaching the sensing electrode(s).

The analyte gas can dissolve in the electrolyte and give rise to a background current which remains after the target gas is removed, resulting in slow response times and background current errors.

This issue is normally overcome in conventional gas sensors by ensuring that all of the target gas is consumed by the sensing electrode (e.g., via capillary limitation of flux to a gas diffusion electrode). However the design of gas diffusion electrodes is complex, especially when using non-aqueous electrolytes such as ionic liquids, and the resulting large surface area and hence double layer capacitance means that dynamic electrochemical techniques such as scanning voltammetry are not feasible.

An example of the current state of the art in microband electrodes are those manufactured by Nanoflex® (http://www.nanoflex.com/Products/Product/Platinum_Substrate) which comprise band electrodes within wells of micrometer dimensions. Previously people have also used line electrode devices deposited on ionic conducting substrates (Kirsi Wallgren, PhD thesis 2005, University of Nottingham and references therein). Microband electrodes can be made via sandwich structures using, for example, micromachined silicon layers or line electrodes on the surface of a substrate. These approaches do not address the issue of ensuring easy gas access to the sensing electrode, since it is immersed within the electrolyte (which may be either a solid or liquid).

In accordance herewith, methods and structures are provided for utilizing microelectrodes and particularly microband electrodes in such a way as to ensure rapid gas access to the sensing electrode(s) and/or to compensate or correct the sensor behavior for variations in the degree to which the sensing electrode is wetted. The attached figures illustrate various aspects of embodiments hereof.

DETAILED DESCRIPTION

The use of non-gas diffusion electrodes in electrochemical gas sensors can alleviate some problematic issues that persist in traditional systems, such as humidity transients, low sensitivity, and slow response times. The novel electrochemical gas sensor described herein includes a sensing electrode fabricated by depositing a catalyst onto a porous support material. The catalyst can be platinum or another noble metal or other catalysts or mixtures thereof known in the art. The porous material can be polytetrafluoroethylene (PTFE) or other porous materials known in the art. This catalyst can be deposited randomly or uniformly. On deposition technique is vacuum sputtering, which when utilized, yields a thin, fully wetted electrode having pores through which a gas can travel. The electrode gives negligible humidity transients when used with an electrolyte such as sulfuric acid, phosphoric acid, ethylmethylimidazolium hydrogen sulfate (EMIM HS) or other known electrolytes or mixtures thereof. The electrode also gives fast response times to hydrogen sulfide gas when used with the above electrolytes.

The electrolyte can be present as a free liquid, absorbed in a wick or separator material, or absorbed in a solid support. The solid support that the electrolyte is absorbed on can be polybenzimidazole film.

FIGS. 1A-1D illustrate aspects of one method of improving on a single, line or band or other type of electrode. One or more sensing electrodes are coated with a meniscus of electrolyte. The upper most electrode rapidly responds to changes in the gas phase due to the thinly wetted electrolyte layer. 'Auxiliary' electrodes deeper into the electrolyte will not respond so quickly and can be used to measure dissolved gas in the bulk of, or spatially varying within, the electrolyte and can then be used to correct the main sensing electrode signal for the effect of these background currents.

This approach requires the shape and location of the electrolyte meniscus to be well defined, which in practice does not always occur—for example changes in temperature and or hydration level of the electrolyte can cause the electrolyte layer to move. By performing measurements such as electrochemical impedance spectroscopy (EIS) on the different electrodes within the structure in FIG. 1A, the position of the electrolyte layer can be determined, and the resulting calculated geometry used in combination with current measurements to compensate for background currents. In extreme cases, the meniscus may even move to the extent that the uppermost electrode is no longer in contact with it, in which case the next electrode down will be used as the sensing electrode.

Figure 1A:
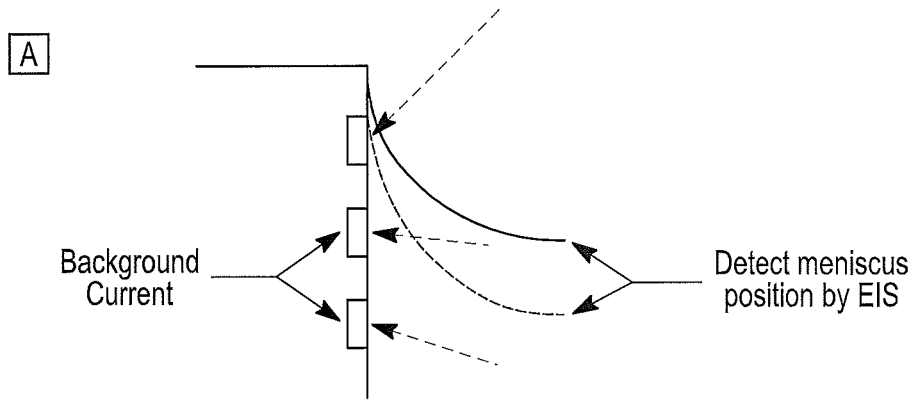
FIG. 1A illustrates an approach for locating the shape and location of the electrolyte meniscus by EIS.
Figure 1B:
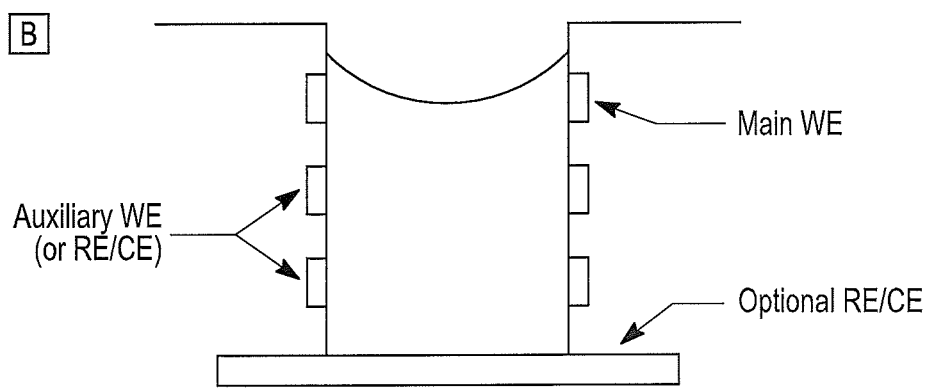
FIG. 1B illustrates a well with layered microband electrodes and counter/reference electrode(s).
Figure 1C:
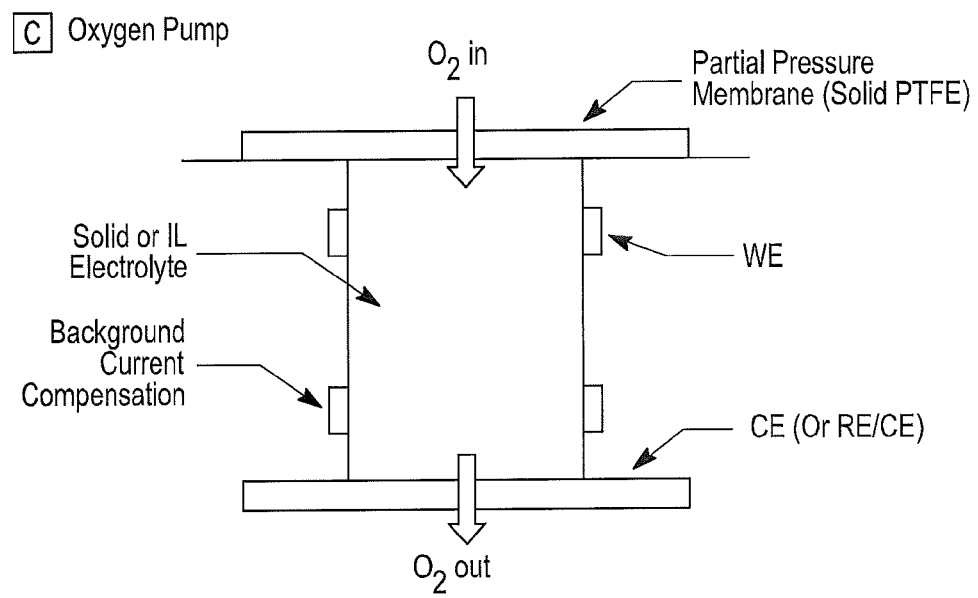
FIG. 1C illustrates an oxygen pump sensor concept.
Figure 1D:
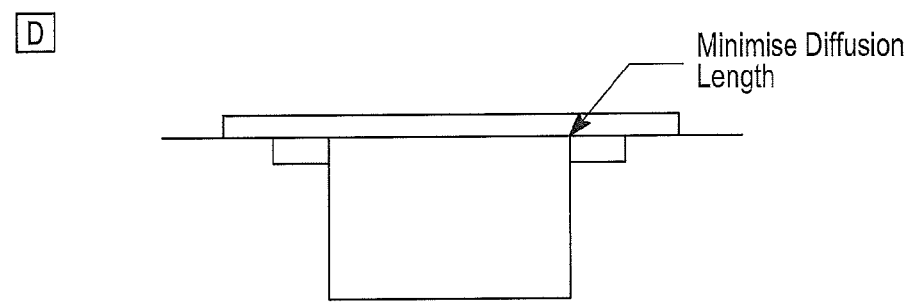
FIG. 1D illustrates a sensing electrode located at the interface between the diffusion barrier and electrolyte.

FIG. 1B illustrates one practical implementation of this approach comprising a well with layered microband electrodes and counter/reference electrode(s). FIG. 1C shows an oxygen pump sensor concept based on a similar approach. An optional solid PTFE oxygen diffusion barrier can be used as a diffusion limiter and/or retainer for liquid electrolyte. The sensing electrode may beneficially be located at the interface between the diffusion barrier and electrolyte as shown in FIG. 1D. The counter electrode may be a conventional gas diffusion electrode or similar for oxygen generation, a further electrode or electrodes may be included to measure and compensate for background currents.

Figure 2A:
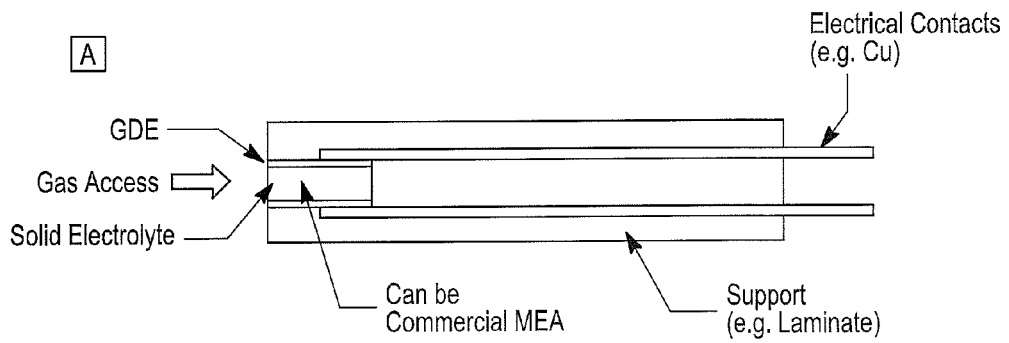
FIG. 2A illustrates a configuration where a solid electrolyte and electrodes such as gas diffusion electrodes are used 'end on' to create a microband type of system.
Figure 2B:
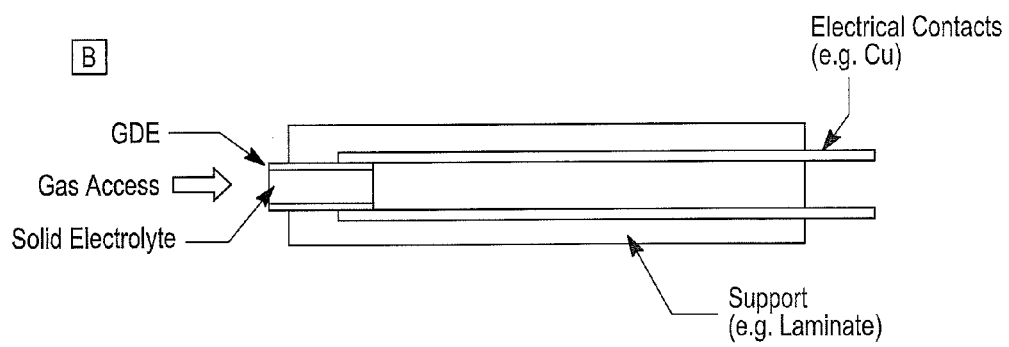
FIG. 2B illustrates a configuration where electrodes and electrolyte protrude from the sensor.
Figure 2C:
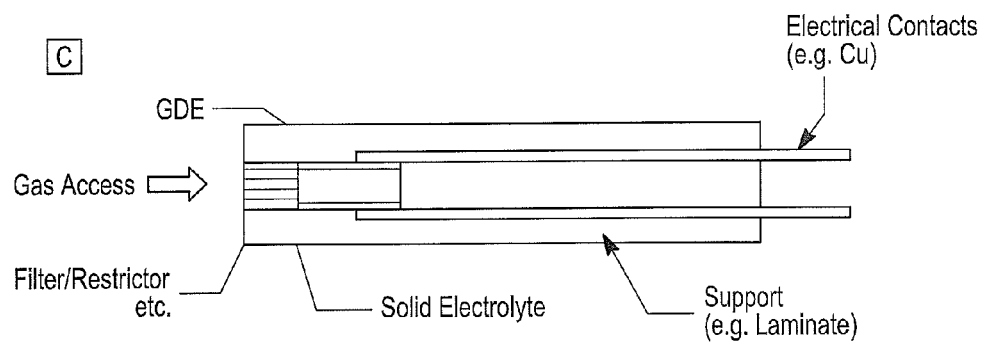
FIG. 2C illustrates a configuration where a solid electrolyte, a filter, and electrodes such as gas diffusion electrodes are used 'end on' to create a microband type of system.
Figure 2D:
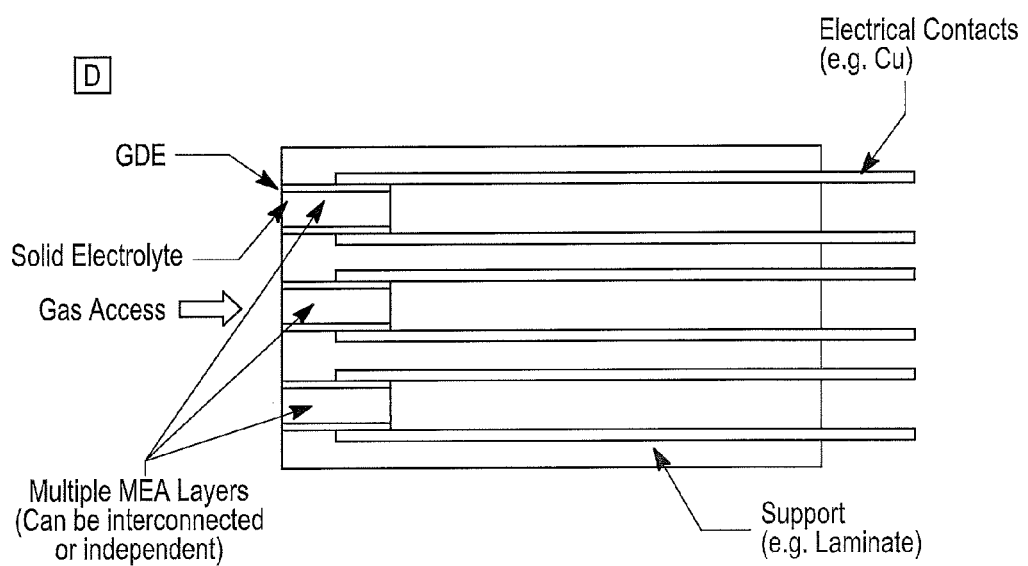
FIG. 2D illustrates a stacked configuration where several solid electrolytes and electrodes, such as gas diffusion electrodes, are used 'end on' to create a microband type of system.

FIG. 2A illustrates a configuration where a solid electrolyte and electrodes such as gas diffusion electrodes are used 'end on' to create a microband type of system. In this case the stack could be implemented with a commercial membrane electrode assembly (MEA) or similar structure. FIG. 2B illustrates that the electrodes and electrolyte could protrude from the sensor and not be flush as in FIG. 2A. Variations on this approach include filters, FIG. 2C, and stacked systems to increase electrode areas as in FIG. 2D.

Structures as described above and illustrated by the attached can be fabricated using, for example, screen printing, MEMS fabrication, multilayer printed circuit boards (e.g., with platinum plated copper), or techniques such as those used for making film and foil capacitors or multilayer batteries.

Figure 3A:
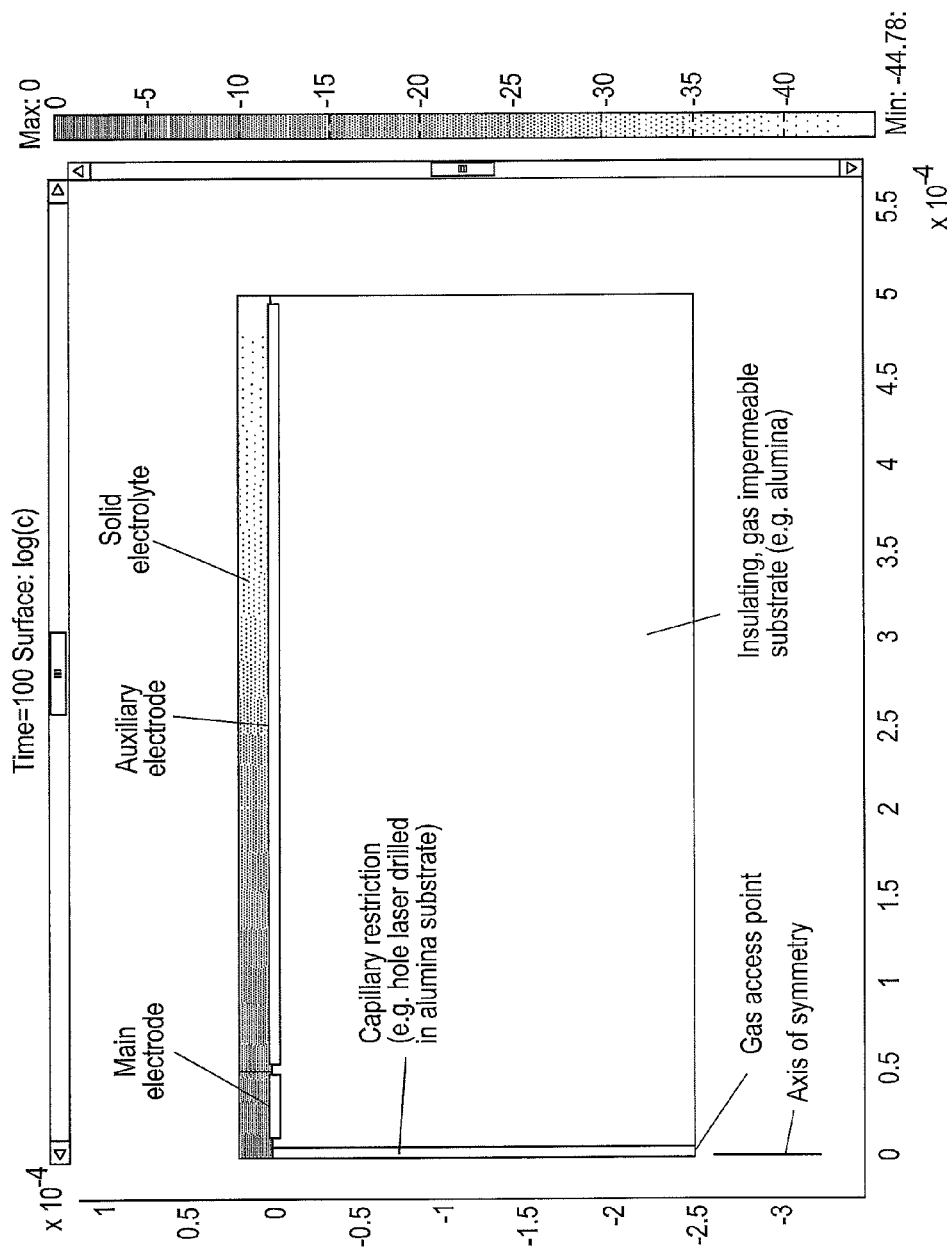
FIG. 3A illustrates a simulated detector's structure.
Figure 3B:
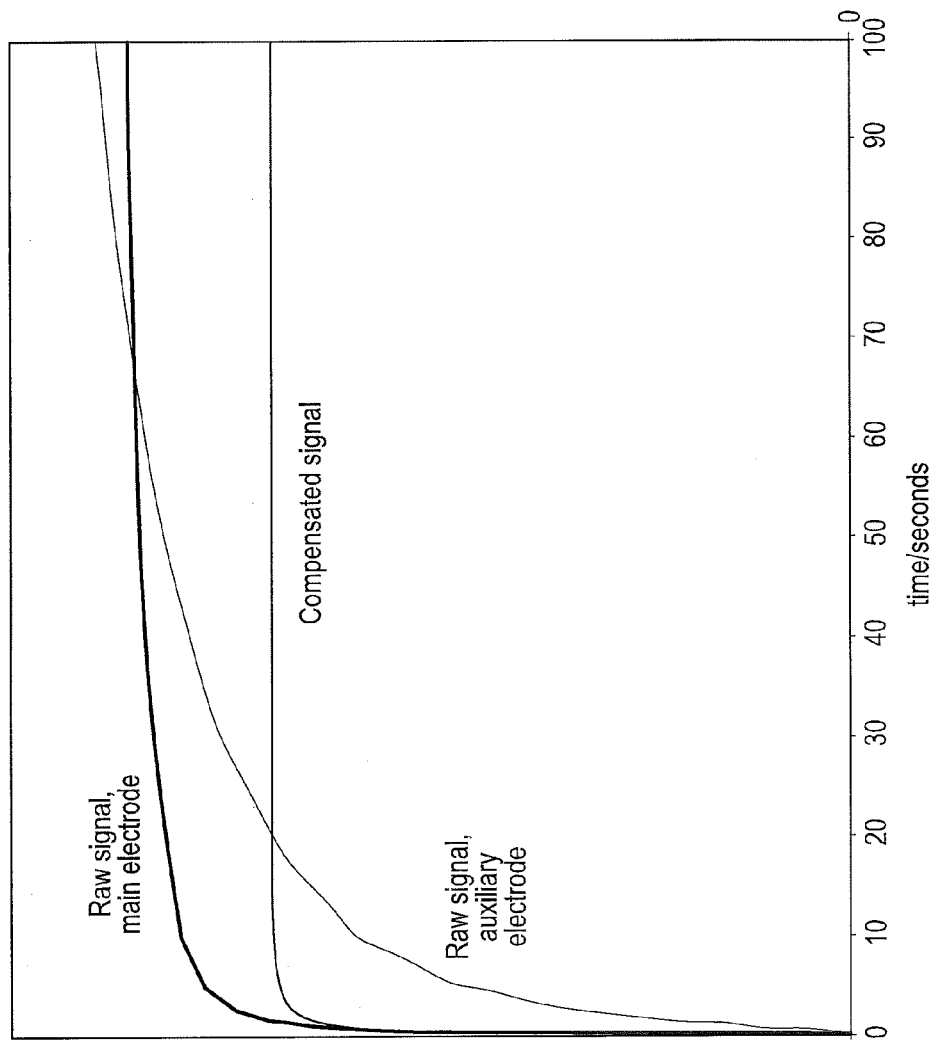
FIG. 3B illustrates expected results of the detector of FIG. 3A.

FIG. 3A illustrates a simulated detector's structure in accordance herewith. FIG. 3B illustrates expected simulated results of the detector of FIG. 3A, namely, the results of a finite element model where the signal from an auxiliary electrode is used to compensate the main electrode signal for the slow secondary response due to dissolved gas.

From the foregoing, it will be observed that numerous variations and modifications may be effected without departing from the spirit and scope of the invention. It is to be understood that no limitation with respect to the specific apparatus illustrated herein is intended or should be inferred. It is, of course, intended to cover by the appended claims all such modifications as fall within the scope of the claims.

Further, logic flows depicted in the figures do not require the particular order shown, or sequential order, to achieve desirable results. Other steps may be provided, or steps may be eliminated, from the described flows, and other components may be add to, or removed from the described embodiments.

We claim:

1. An electrochemical gas detector comprising:
   a well;
   a plurality of layered microband electrodes disposed about and in contact with an interior of the well, wherein the plurality of layered microband electrodes comprise individual working electrodes;
   an electrolyte disposed within the well, wherein a first microband electrode of the plurality of microband electrodes is coated with a meniscus of the electrolyte, and wherein at least a second microband electrode of the plurality of microband electrodes is coated with a bulk of the electrolyte within the well; and
   at least one of a counter electrode or a reference electrode in contact with the electrolyte.

2. The electrochemical gas sensor of claim 1, wherein each microband electrode of the plurality of layered microband electrodes comprises a catalyst, and wherein the catalyst comprises platinum or another noble metal.

3. The electrochemical gas sensor of claim 1, wherein the electrolyte comprises sulfuric acid, phosphoric acid, or ethylmethylimidazolium hydrogen sulfate.

4. The electrochemical gas sensor of claim 1, wherein the electrolyte comprises a free liquid.

5. The electrochemical gas sensor of claim 1, wherein the electrolyte comprises sulfuric acid.

6. The electrochemical gas sensor of claim 1, wherein the electrolyte comprises phosphoric acid.

7. The electrochemical gas sensor of claim 1, wherein the electrolyte comprises ethylmethylimidazolium hydrogen sulfate.

8. The electrochemical gas sensor of claim 2, wherein the catalyst comprises platinum.

9. The electrochemical gas sensor of claim 2, wherein the catalyst comprises platinum, and wherein the electrolyte comprises phosphoric acid.

10. The electrochemical gas sensor of claim 2, wherein the catalyst comprises platinum, and wherein the electrolyte comprises sulfuric acid.

11. The electrochemical gas sensor of claim 2, wherein the catalyst comprises platinum, and wherein the electrolyte comprises ethylmethylimidazolium hydrogen sulfate.

12. The electrochemical gas sensor of claim 1, where the electrolyte comprises one of an aqueous liquid or an ionic liquid.

13. The electrochemical gas sensor of claim 1, wherein the first microband electrode of the plurality of layered microband electrodes is a sensing electrode.

14. The electrochemical gas sensor of claim 13, wherein the at least second microband electrode of the plurality of layered microband electrodes is a second sensing electrode, wherein the second sensing electrode is configured to respond to measured dissolved gas in a bulk of, or spatially varying within the electrolyte, to correct the signal of the first sensing electrode for an effect of background currents.

15. The electrochemical gas sensor of claim 1, further comprising an oxygen diffusion barrier or retainer configured to maintain the electrolyte in the well, wherein a sensing electrode is located at an interface between the diffusion barrier and the electrolyte.

* * * * *

UNITED STATES PATENT AND TRADEMARK OFFICE
CERTIFICATE OF CORRECTION

PATENT NO.         : 10,006,881 B2
APPLICATION NO.    : 14/275037
DATED              : June 26, 2018
INVENTOR(S)        : Pratt et al.

Page 1 of 1

It is certified that error appears in the above-identified patent and that said Letters Patent is hereby corrected as shown below:

Column 4/Line 13: "hand electrodes" should be "band electrodes"

Signed and Sealed this
Fourth Day of December, 2018

Andrei Iancu
*Director of the United States Patent and Trademark Office*